US006364868B1

(12) United States Patent
Ikeguchi

(10) Patent No.: US 6,364,868 B1
(45) Date of Patent: Apr. 2, 2002

(54) URETERAL CATHETER AND TISSUE EXPANDER AND METHOD OF MEGAURETER CREATION

(75) Inventor: Edward F. Ikeguchi, Larchmont, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/827,334

(22) Filed: Mar. 26, 1997

Related U.S. Application Data

(63) Continuation-in-part of application No. 08/510,555, filed on Aug. 2, 1995, now abandoned.

(51) Int. Cl.⁷ .............................................. A61M 31/00
(52) U.S. Cl. ...................... 604/514; 604/8; 604/96.01; 604/104; 604/544
(58) Field of Search ........................... 604/19, 27, 43, 604/280, 281, 282, 264, 93, 98, 101, 104, 105, 265, 8–10, 54, 55, 49, 96, 97, 317, 326, 327–329, 331, 334, 349, 351, 352, 403, 408, 94.01, 102.01, 284, 540, 541, 544, 523, 524, 530, 98.01, 101.1, 101.04, 101.05, 93.01, 514, 500, 515, 517, 96.01, 9; 128/898; 606/191, 192, 193, 198

(56) References Cited

U.S. PATENT DOCUMENTS

| | | | |
|---|---|---|---|
| 4,217,889 A | | 8/1980 | Radovan et al. |
| 4,265,243 A | * | 5/1981 | Taylor ........................ 604/128 |
| 4,800,901 A | * | 1/1989 | Rosenberg .................. 128/899 |
| 4,813,925 A | | 3/1989 | Anderson, Jr. et al. |
| 4,911,163 A | | 3/1990 | Fina |
| 4,930,496 A | | 6/1990 | Bosley, Jr. |
| 4,932,938 A | * | 6/1990 | Goldberg et al. .............. 604/96 |
| 4,950,228 A | | 8/1990 | Knapp, Jr. et al. |
| 5,019,102 A | * | 5/1991 | Hoene ......................... 604/264 |
| 5,083,576 A | | 1/1992 | Ruiz-Razura et al. |
| 5,092,348 A | | 3/1992 | Dubrul et al. |
| 5,109,875 A | | 5/1992 | Gottlieb |
| 5,165,425 A | | 11/1992 | Vermot |
| 5,246,445 A | | 9/1993 | Yachia et al. |
| 5,250,070 A | * | 10/1993 | Parodi ......................... 604/96 |
| 5,263,931 A | * | 11/1993 | Miller ......................... 604/96 |
| 5,328,471 A | | 7/1994 | Slepian |
| 5,417,657 A | * | 5/1995 | Hauer ......................... 604/101 |
| 5,425,760 A | | 6/1995 | Rosenberg |
| 5,501,669 A | * | 3/1996 | Conway et al. .............. 604/328 |
| 5,562,622 A | * | 10/1996 | Tihon ......................... 604/329 |
| 5,681,274 A | * | 10/1997 | Perkins et al. .............. 604/264 |
| 5,695,457 A | * | 12/1997 | St. Goar et al. ............ 604/280 |

FOREIGN PATENT DOCUMENTS

WO    96/12518    2/1996

OTHER PUBLICATIONS

J.N. Kabolin, "Anatomy of the Retroperitoneum and Kidney", *Campbell's Urology*, Ed.6, W.B. Saunders Co., 1992, pp. 3, 36–40.

L.R. King, "Vesicoureteral Reflux, Magaureter, and Ureteral Reimplantation", *Campbell's Urology*, pp. 1689–1742.

(List continued on next page.)

*Primary Examiner*—Ronald K. Stright, Jr.
(74) *Attorney, Agent, or Firm*—Cowan, Liebowitz & Latman, P.C.; William H. Dippert

(57) ABSTRACT

An apparatus and method of producing a megaureter for purposes of expanding the native urothelium of the ureter to be used in various types of urinary tract reconstruction. A unique ureteral catheter which may be placed either transurethrally or percutaneously, comprising a urinary drainage tube combined with a tissue expander.

5 Claims, 14 Drawing Sheets

OTHER PUBLICATIONS

W.S. McDougal, "Use of Intestinal Segments in the Urinary Tract: Basic Principles", *Campbell's Urology*, pp. 2630–2653 pp. 2595–2629.

M.E. Mitchell et al., "Augmentation Cystoplasty Implantation of Artificial Urinary Sphincter in Men and Women and Reconstruction of the Dysfunctional Urinary Tract", *Campbell's Urology*, pp. 2630–2653.

Churchill, B.M., et al., "Ureteral Bladder Augmentation", *Journal of Urology*, 150: 716–720, Aug. 1993.

Hitchcock, R.J., et al., "Ureterocystoplasty: The 'Bladder' Augmentation of Choice", *British Journal of Urology*, 73 (5): 575–579, 1994.

Manders, E.K., et al., "Elongation of Peripheral Nerve and Viscera Containing Smooth Muscle." *Clinics in Plastic Surgery*, vol. 14, No. 3, 551–562, Jul. 1987.

\* cited by examiner

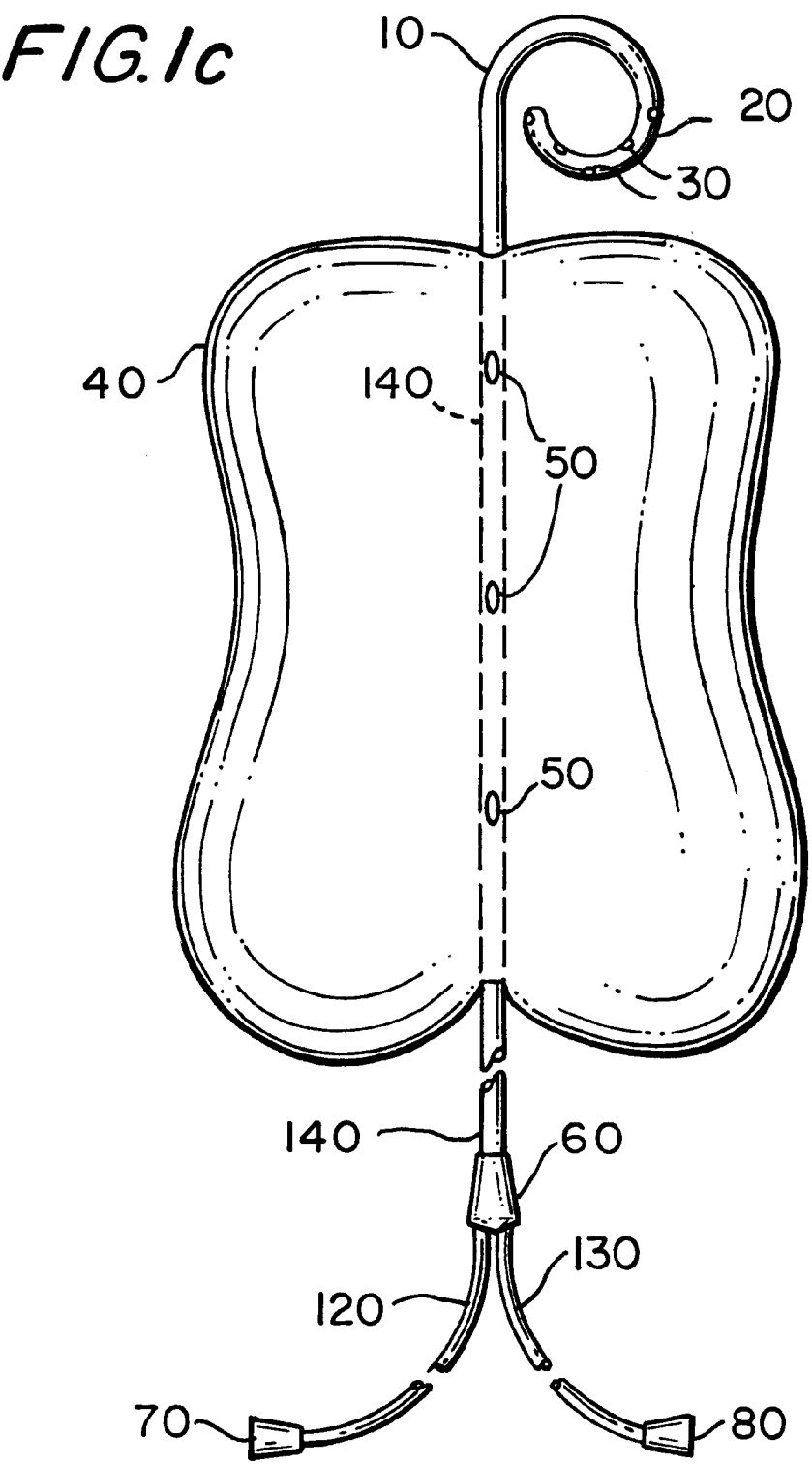

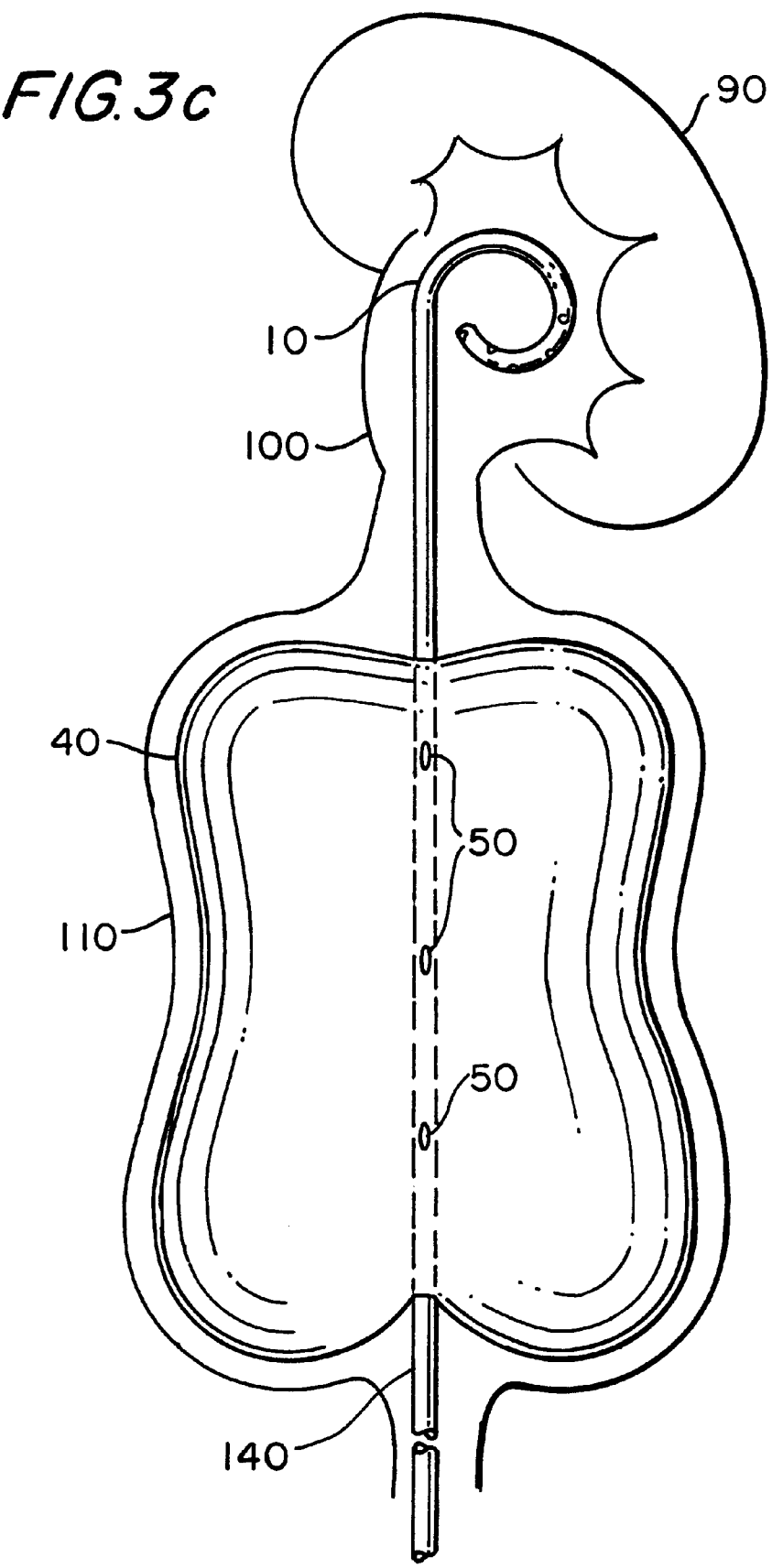

URETERAL CATHETER AND TISSUE EXPANDER AND METHOD OF MEGAURETER CREATION

CROSS-REFERENCE TO RELATED APPLICATION

This application is a continuation-in-part of U.S. patent application Ser. No. 08/510,555, filed Aug. 2, 1995, now abandon, which is based upon Disclosure Document No. 378873 submitted to the U.S. Patent and Trademark Office and received Jun. 5, 1995.

FIELD OF THE INVENTION

This invention relates to a device and method by which a human ureter may be made to expand to form what is known as a megaureter. In addition, this invention describes a device which will accomplish this without injury to the kidney.

BACKGROUND OF THE INVENTION

The term "megaureter" refers to a large, ectatic, dilated ureter, a condition may be congenital or acquired. It is the end result of increased hydrostatic pressure in the ureter from obstruction to the flow of urine, reflux of urine from the bladder back into the ureter (known as vesicoure-teral reflux), or for reasons unknown (i.e., idiopathic). Although megaureter is considered to be a pathologic condition, current medical advances in the field of urinary tract reconstruction have led to the recognition of certain circumstances in which the existence of a megaureter is desirable. A detailed description of urinary tract anatomy and the fundamentals of megaureter may be found in J. N. Kabolin, "Anatomy of the Retroperitoneum and Kidney", *Campbell's Urology*, Ed.6, W. B. Saunders Co., 1992, pp. 3, 36–40 and L. R. King, "Vesicoureteral Reflux, Magaureter, and Ureteral Reimplantation", *Campbell's Urology*, pp. 1689–1742.

Yearly, several thousand individuals undergo surgical reconstruction of the urinary tract. Reasons for requiring urinary tract reconstruction vary greatly and include: cancers of the urinary tract such as bladder or ureter, congenital defects such as bladder exstrophy, and poorly compliant, small capacity bladders (causing urinary incontinence and renal failure) often seen in paraplegics or patients with posterior urethral valves. The surgical procedures performed vary greatly, though common to all these procedures is the frequent necessity of utilizing segments of the gastrointestinal tract in the reconstructive process.

In the past virtually all segments of the gastrointestinal tract have been used successfully in the reconstruction of the urinary tract. Unfortunately, the incorporation of tissue from the gastrointestinal tract into the urinary tract predisposes the patient to several problems. These problems involve anatomic and physiologic deficiencies of the gastrointestinal tract subsequent to the removal of various lengths of intestine (i.e., malabsorption, diarrhea, and vitamin or bile salt deficiencies). Also, problems inherent in combining the gastrointestinal and urinary tracts include mucous production by intestinal mucosa, enhanced bacterial growth with frequent urinary tract infections, pyelonephritis, abnormal electrolyte and acid reabsorption, urinary stone formation, and occasionally even cancer formation. Further descriptions and fundamentals of urinary tract reconstruction (i.e., urinary diversion and bladder augmentation) can be found in *Campbell's Urology:* W. S. McDougal, "Use of Intestinal Segments in the Urinary Tract: Basic Principles", pp. 2595–2629, and M. E. Mitchell et al., "Augmentation Cystoplasty Implantation of Artificial Urinary Sphincter in Men and Women and Reconstruction of the Dysfunctional Urinary Tract", pp. 2630–2653.

Extensive research has been carried out in an effort to identify an alternative to the gastrointestinal tract in the reconstruction of the urinary system. Ideas have included use of muscle flaps and fascia, harvesting cells of the urinary tract (i.e., urothelium) and cultivating them over bio-absorbable polymers, and transplantation of urothelium from human donors or animals. To date these approaches and others have been seuboptimal.

Recently, however, several medical investigators, have described the use of native urothelium from megaureters to reconstruct the urinary tract (Churchill, B. M., Aliabadi, H., Landau, E. H., McLorie, G. A., Steckler, R. E., McKenna, P. H., Khoury, A. E. "Ureteral Bladder Augmentation", *Journal of Urology*, 150: 716–720, 1993; Hitchcock, R. J., Duffy, P. G., Malone, P. S., "Ureterocystoplasty: The 'Bladder' Augmentation of Choice", *British Journal of Urology*, 73(5): 575–579, 1994). Each of these authors concluded that when possible, bladder augmentation using ureteral tissue from dilated ureters yielded the best outcome, with reduction in the complications common to all reconstructions utilizing the intestinal tract. of course, the feasibility of this operation was contingent upon the patient already having a megaureter. Thus, their experience was restricted to those select patients who, ironically, were "fortunate" enough to have the pathologic entity of megaureter. Unfortunately, this represents only a small fraction of the population in need of urinary tract reconstruction. Also, since most of these patients had poorly functioning kidneys associated with megaureter, nephrectomy (i.e., removal of the kidney) or partial nephrectomy (i.e., removal of a portion of the kidney) was performed in the majority of cases reported.

Thus, there is a need to develop a device and method by which a megaureter could be produced in a controlled, monitored setting while maintaining the physiologic integrity of the associated kidney. To date there is no known device or method which will allow a megaureter to be produced iatrogenically without jeopardizing the kidney in a patient requiring urinary tract reconstruction. This could be accomplished with the invention described below which is a method utilizing a ureteral catheter which combines a urinary drainage tube and a tissue expander.

Tissue expanders are reservoirs which can contain varying volumes of either gaseous or liquid materials. Usually constructed of rubber, latex, or silicone elastomers, tissue expanders are extremely pliable, enabling them to be filled to very large volumes while maintaining low pressures within the reservoirs themselves. To date, the most common use of tissue expanders is in the field of plastic surgery, where they are often implanted under the skin and gradually (i.e., over the course of weeks to months) expanded to stretch the overlying skin. Once the tissue is stretched to the desired surface area, the tissue expander may then be deflated and removed. The overlying stretched skin can then be used to cover many types of large wounds ranging from those rendered with the excision of large unsightly scars or tattoos to wounds sustained in avulsion injuries, amputations, or burns.

Tissue expanders differ from the simple "balloons" placed at the ends of conventional urinary catheters (e.g., the "Foley" catheter), which serve the purpose of maintaining a catheter in a certain position or preventing a catheter from becoming dislodged. Also, several ureteral catheters which incorporate balloons are currently in production. For instance, the Microvasive Corporation of Natick, Mass. produces several ureteral dilation products. However, these catheters are not meant to dilate the ureter slowly over several days, weeks, or even months under low pressures (i.e., below diastolic pressure) to achieve large volumes (i.e., three to six hundred milliliters or volumes comparable to normal human bladder capacity) but, rather, are meant to rapidly dilate the ureter to allow stones to pass, rupture strictures in the wall of the ureter, or allow passage of larger bore ureteral instruments. Microvasive's product catalogues describe the nature of the balloons on the ureteral dilation catheters as "noncompliant," able to withstand dilation pressures of up to ten or more atmospheres while maintaining balloon diameters ranging from four to ten millimeters.

Tissue expanders have fluid reservoirs which function as carriers of large capacities while maintaining low pressures inside the walls of the reservoirs themselves. This unique property of tissue expanders, which is attributable to the extremely elastic and complaint substance from which they are made (usually silicone elastomer), is an important feature that is crucial in preventing the ischemia and necrosis of surrounding tissue. So unique is this quality of tissue expanders that a multitude of patents have been issued for various tissue expanders and breast protheses. For instance, U.S. Pat. No. 4,217,889 issued Aug. 19, 1980 to Radovan et al. and entitled "Flap Development Device and Method of Progressively Increasing Skin Area", describes a continuous fluid-tight envelope with a chamber therein . . . whereby the volume of the envelope is determinable as a function of the amount of fluid contained in the chamber . . . " and "the method of progressively enlarging over a prolonged period of time the area of skin and subcutaneous layer overlaying a reference area . . . "

Another example is U.S. Pat. No. 5,092,348 issued Mar. 3, 1992 to Dubrul et al. and entitled "Textured Tissue Expander". The abstract states that, "The textured surface is expected to decrease subsequent capsular contracture and provide a non-skid surface to hold the device in position and permit differential expansion."

Tissue expansion of the ureter has been described in the past (Manders, E. K., et al.) "Elongation of Peripheral Nerve and Viscera Containing Smooth Muscle." *Clinics in Plastic Surgery*, Vol. 13, No. 3, July 1987). This was performed experimentally in dogs by the placement of a rectangular tissue expander posterior and external to the ureter in the retroperitoneal space. This is not practical in clinical practice since placement of a tissue expander external to and behind the ureter would require an extensive open surgical procedure as well as a second operation to remove the apparatus. There is no known research that has ever been performed in the placement and use of a tissue expander inside the lumen of the ureter. Such a device could be installed and removed through the urethra endoscopically or percutaneously via an access tract to the renal pelvis in the patient's back (i.e., a percutaneous nephrostomy).

SUMMARY OF THE INVENTION

The present invention is directed to a device and method by which a megaureter may be produced without compromising the function of the associated kidney. A ureteral catheter for iatrogenically producing a megaureter is comprised of a tissue expander and a drainage tube. The tissue expander comprises a tissue expander conduit with a tissue expander reservoir on the distal end of the conduit and with a first lumen extending from the proximal end of the conduit to inside the reservoir to allow inflation of the reservoir. The drainage tube has a lumen extending at least from the proximal end of the reservoir and out the distal end of the reservoir, the drainage tube lumen having a plurality of holes in its distal end. The reservoir circumferentially surrounds at least a portion of the drainage tube, and the first lumen has an infusion port connected thereto at its proximal end. The excess urothelium produced in the process of tissue expansion can then be used in reconstruction of the urinary tract.

BRIEF DESCRIPTION OF THE FIGURES

In the drawings, closely related figures have the same number but diff t alphabetic suffixes.

FIGS. 1a–1c are partly cross-sectional views of an embodiment of the invention with a single curl and the tissue expander component, in varying degrees of inflation;

FIGS. 2a–2f each represent a perpendicular cross-section of the embodiment shown in FIG. 1a;

FIGS. 3a–3c each represent a partly cross-sectional view of an embodiment of the invention inserted into the urinary tract transurethrally with the tissue expander component in varying degrees of inflation;

DETAILED DESCRIPTION OF THE INVENTION

Figure 1A:
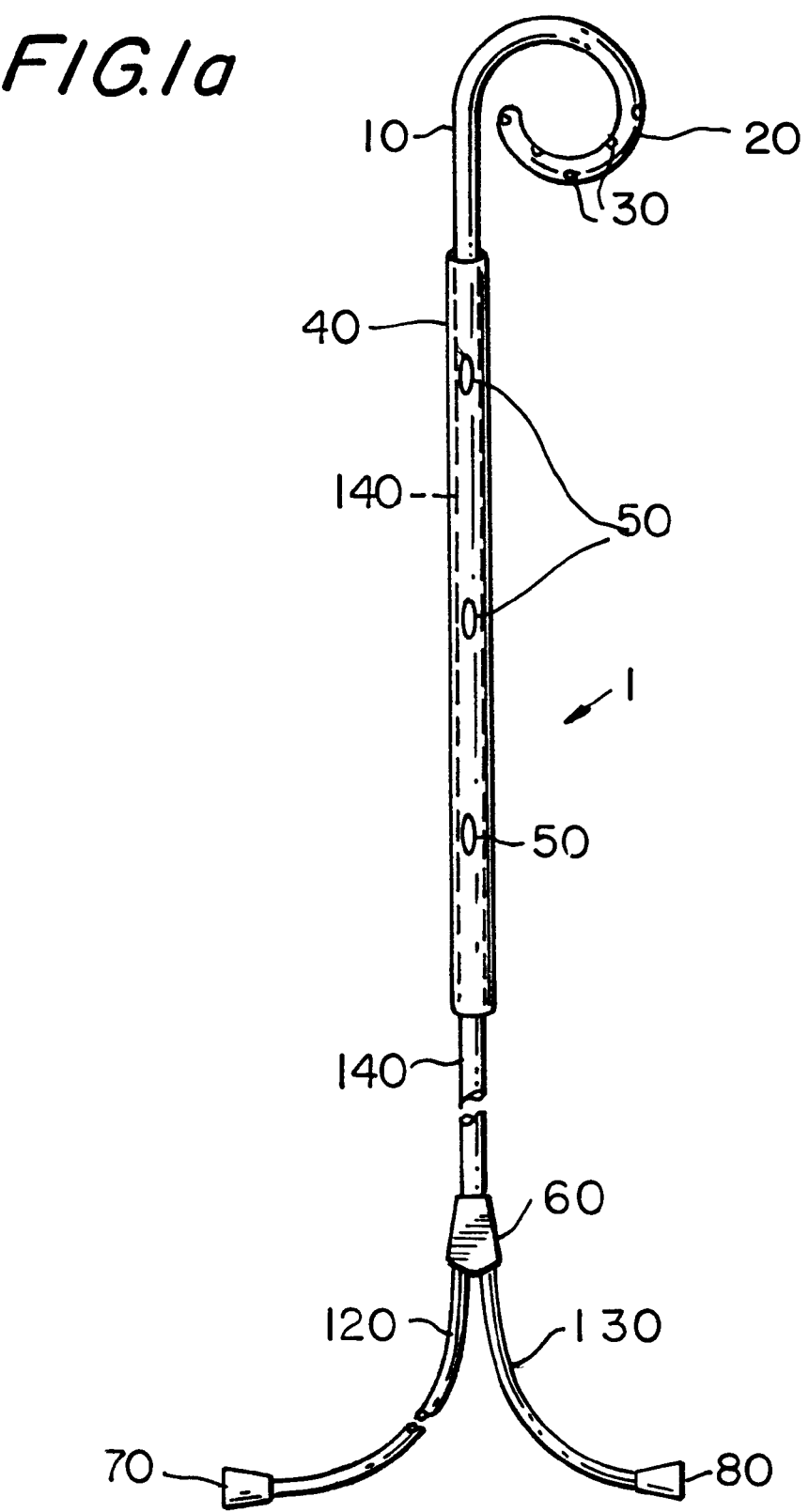

This invention herein concerns a device and method by which a megaureter may be produced in an induced iatrogenic fashion. Although megaureter is usually associated with damage to the ipsilateral kidney, the invention described below allows production of a megaureter without injury to the kidney. Since a simple tissue expander placed into the ureter would obstruct the flow of urine and subsequently damage the associated kidney, this invention incorporates a urinary drainage tube to allow the free flow of urine from the level of the kidney to the bladder or exterior.

Thus, with the invention described herein, a patient in need of urinary tract reconstruction could initially have a megaureter produced over several weeks. The large dilated ureter could then provide ample native urothelium to be harvested for urinary tract reconstruction. Throughout the course of tissue expansion, urine could flow unobstructed, thereby preserving renal function.

The invention can perhaps be better appreciated by reference to drawings herein. FIGS. 1 to 9 are illustrations of a combination urinary drainage tube and tissue expander according to the present invention. FIGS. 1 and 2a–2f shows a combined apparatus 1 with a urinary drainage tube which is comprised of a distal urine drainage tube 10 with a preferred curled end 20 containing urine drainage holes 30, a urine drainage tube lumen 190 which extends to the proximal urine drainage tube 120 and the urine drainage port 70. A urine collection bag 72 is provided. A tissue expander is comprised of a tissue expander reservoir 40, an inner aspect of which is in fluid communication with a tissue expander conduit 130 and its tissue expander conduit lumen 200 via tissue expander infusion holes 50, ultimately ending with a tissue expander infusion port 80.

Figure 1B:
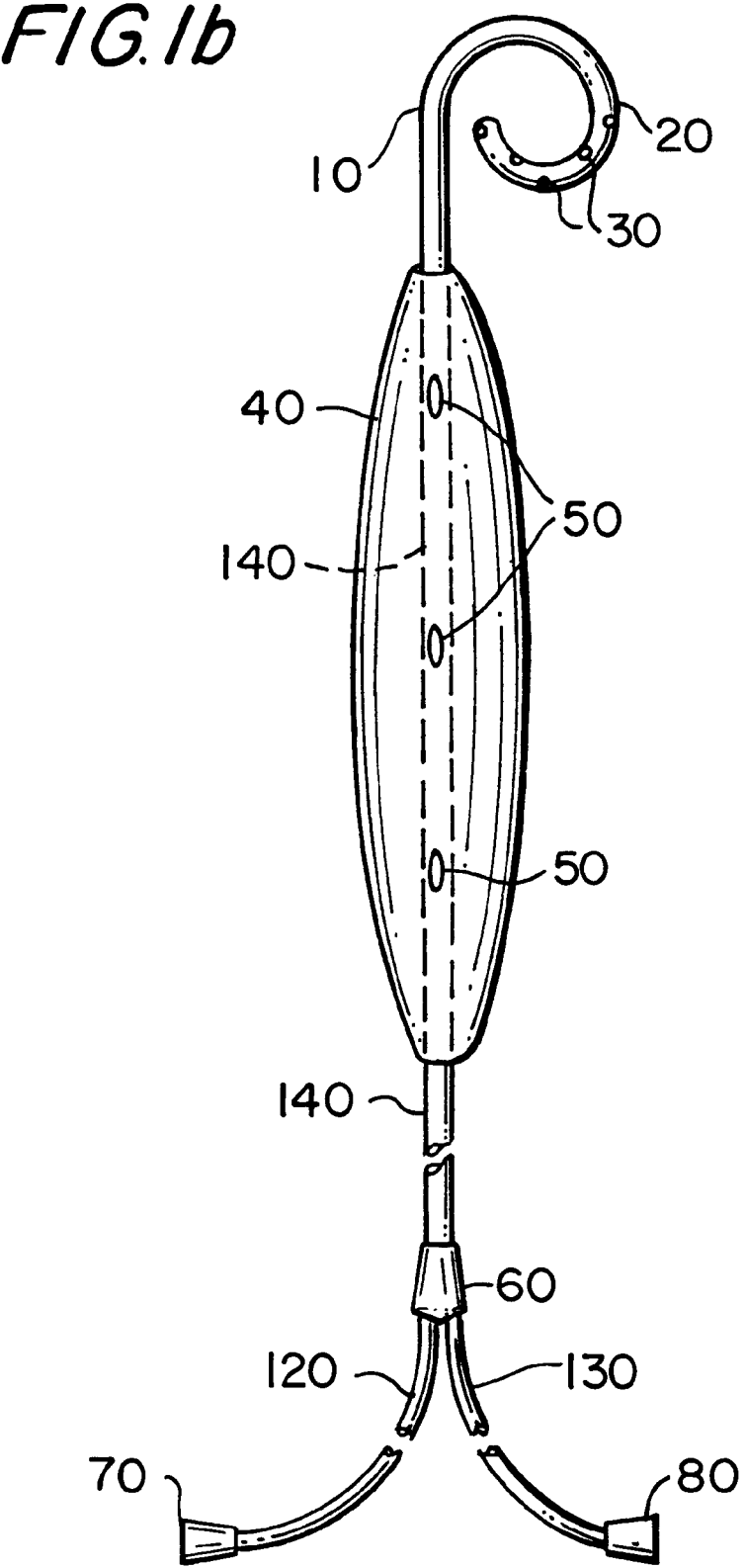
Figure 2:
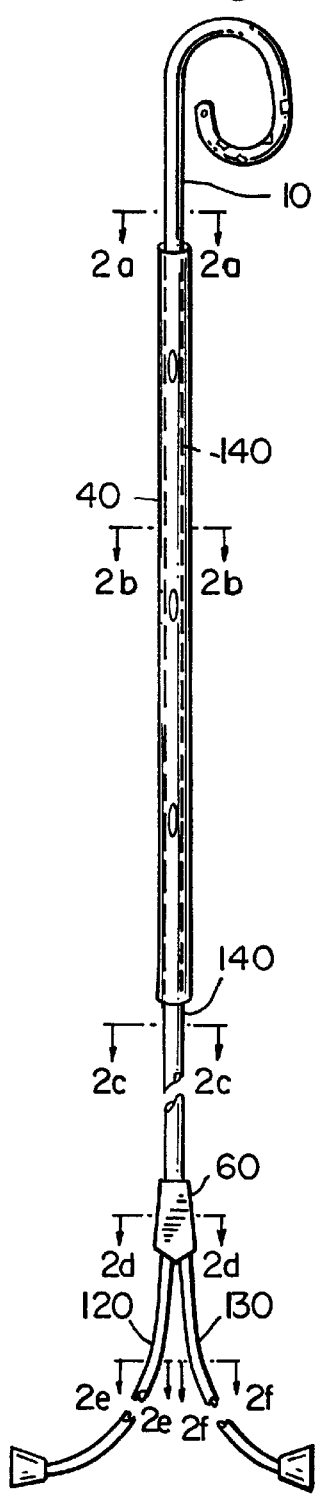
Figure 2A:
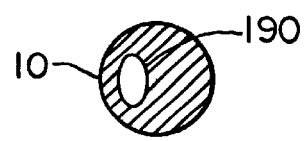
Figure 2B:
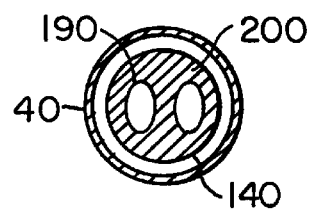
Figure 2C:
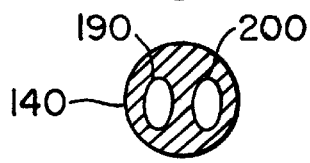
Figure 2D:
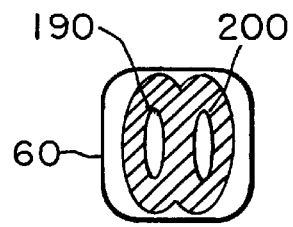
Figure 2E:
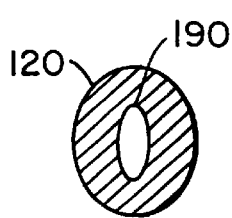
Figure 2F:
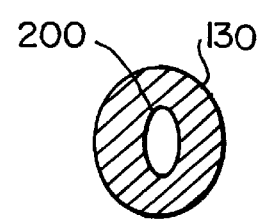

FIGS. 1*a* to 1*c* illustrate the present invention with the tissue expander reservoir in various degrees of filling. The urinary drainage tube is made of a material with qualities such that the tube is flexible but does not easily kink or collapse, preferably plastic or silicone. In a preferred embodiment, the distal urine drainage tube 10 ends in a curl 20 such that the catheter remains securely lodged in the renal pelvis 100. The curl 20 preferably constitutes at least a 360° curve or a coil at the distal end of the drainage tube 10. The curl decreases any tendency of the drainage tube to dislodge or irritate the surrounding tissue. The curled end of the urinary, drainage tube 20 contains multiple holes 30 to allow for the drainage of urine. The proximal urine drainage tube 120 may be long enough to be brought out externally through the urethra 180 to drain into a collection bag 72.

The tissue expander reservoir 30 is preferably textured on the external surfare 42, to enhance griping of the tissue to be expanded. The reservoir bag is preferably made of rubber latex or silicone elastomer 44 having coating of low friction lubricant 46.

The tissue expander reservoir 40 is attached in a side by side fashion to the urinary drainage tube. In a preferred embodiment, the tissue expander reservoir 40 is attached to surround the urinary drainage tube circumferentially along a given length of the urinary drainage tube corresponding to the desired length of ureter 110 to be expanded. Since the drainage tube goes through the center of the expander reservoir, there is no displacement of the catheter regardless of how large the balloon is inflated. The tissue expander reservoir 40 is situatable at various sites along the length of the urinary drainage tube to allow specific portions of the ureter to be chosen for expansion (i.e., the proximal, mid-, or distal ureters). The reservoir is accordingly adjustable along the length of the urinary drainage tube so that a selected portion of the urethra can be expanded. The tissue expander reservoir 40 is comprised of a material which will be able to accommodate volumes comparable to normal human bladder capacities (i.e., 300 cc to greater than 600 cc) without producing pressures within the tissue expander reservoir 40 greater than normal human diastolic pressures (i.e., no greater than 60 to 80 mm Hg.), preferably a material such as an elastic rubber, latex, or a silicone elastomer. This is a critical characteristic of the tissue expander reservoir 40 since higher pressures may result in ischemia and necrosis of the surrounding ureter.

The tissue expander reservoir 40 is inflated or deflated by infusing a fluid, said fluid being either liquid (e.g., water) or gas (e.g., air), through an infusion port 80 which communicates with the interior of the tissue expander reservoir 40 via the tissue expander conduit 130. In a preferred embodiment there are several tissue expander infusion holes 50 situated in the conduit 130 along the length of the tissue expander reservoir 40 to assure uniform filling and emptying of the tissue expander reservoir 40. Uniform expansion of the reservoir results in a uniform and acceptable megaureter.

The ureteral catheter contains a catheter consolidation site 60 at which point both the urine drainage tube 120 and tissue expander conduit 130 are incorporated into a single catheter 140. It should be noted, however, that the combined urine drainage tube and tissue expander conduit 140 accordingly has two lumens corresponding to the urine drainage tube lumen 190 and the tissue expander conduit lumen 200 (see FIGS. 2*c*–2*f*).

Figure 9:
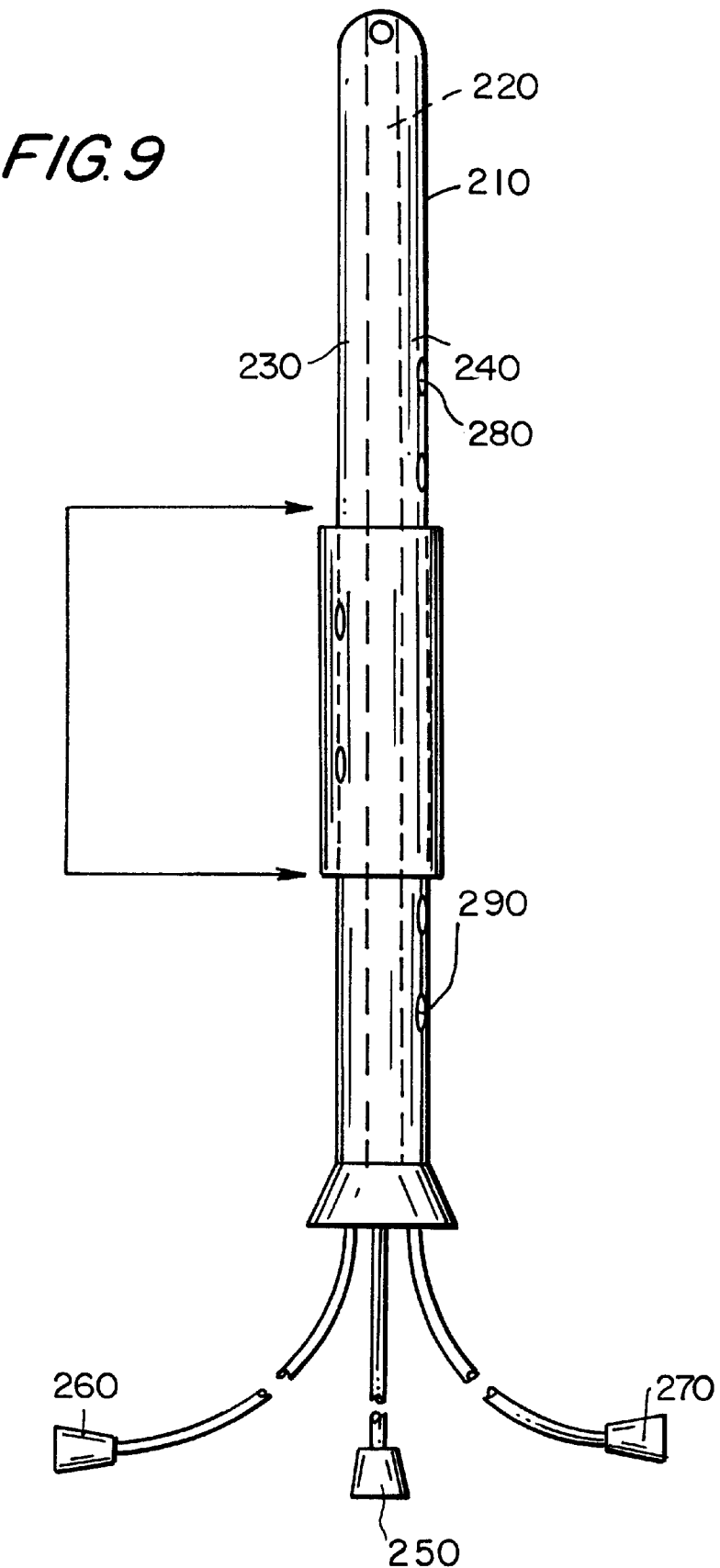
FIG. 9 represents an embodiment of the invention having three lumens.

In alternative embodiments of the invention, there could be more than two lumens, as shown in FIG. 9, discussed below. It is understood that one or more lumens could be integrated into the combined catheter to accommodate a variety of additional functions. Each lumen within the combined urine drainage tube and tissue expander conduit 140 continues to serve its individual and unique function. The drainage tube lumen continues to act as a drainage means for urine and the expander conduit continues to act as means for expanding the reservoir.

FIGS. 2*a*–2*f* illustrate the relationships of various structures in cross section including the distal urine drainage tube 10 with the urine drainage tube lumen 190, the tissue expander reservoir 40 surrounding the combined urine drainage tube and tissue expander conduit 140, which is comprised of both the urine drainage tube lumen 190 and tissue expander conduit lumen 200, and the catheter consolidation site 60, which combines the proximal urine drainage tube 120 and the tissue expander conduit 130.

Figure 3A:
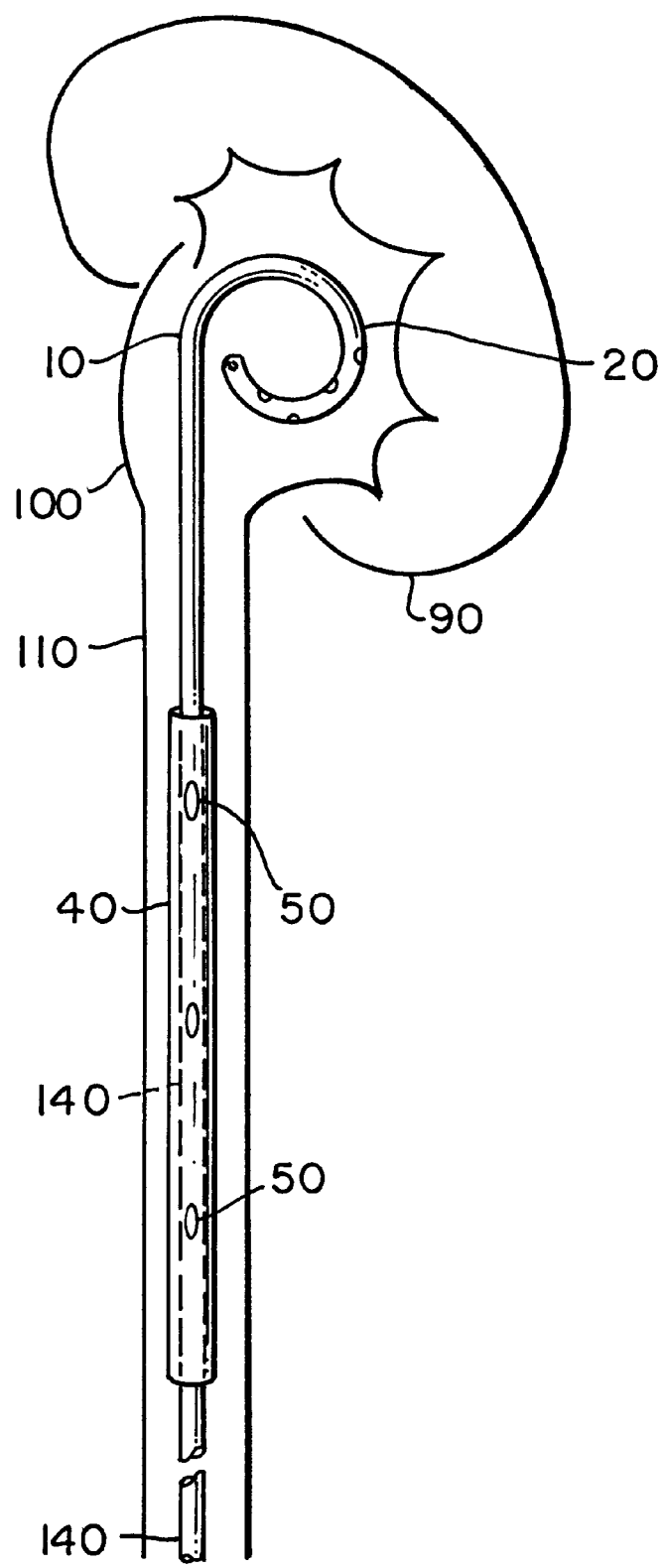
Figure 3B:
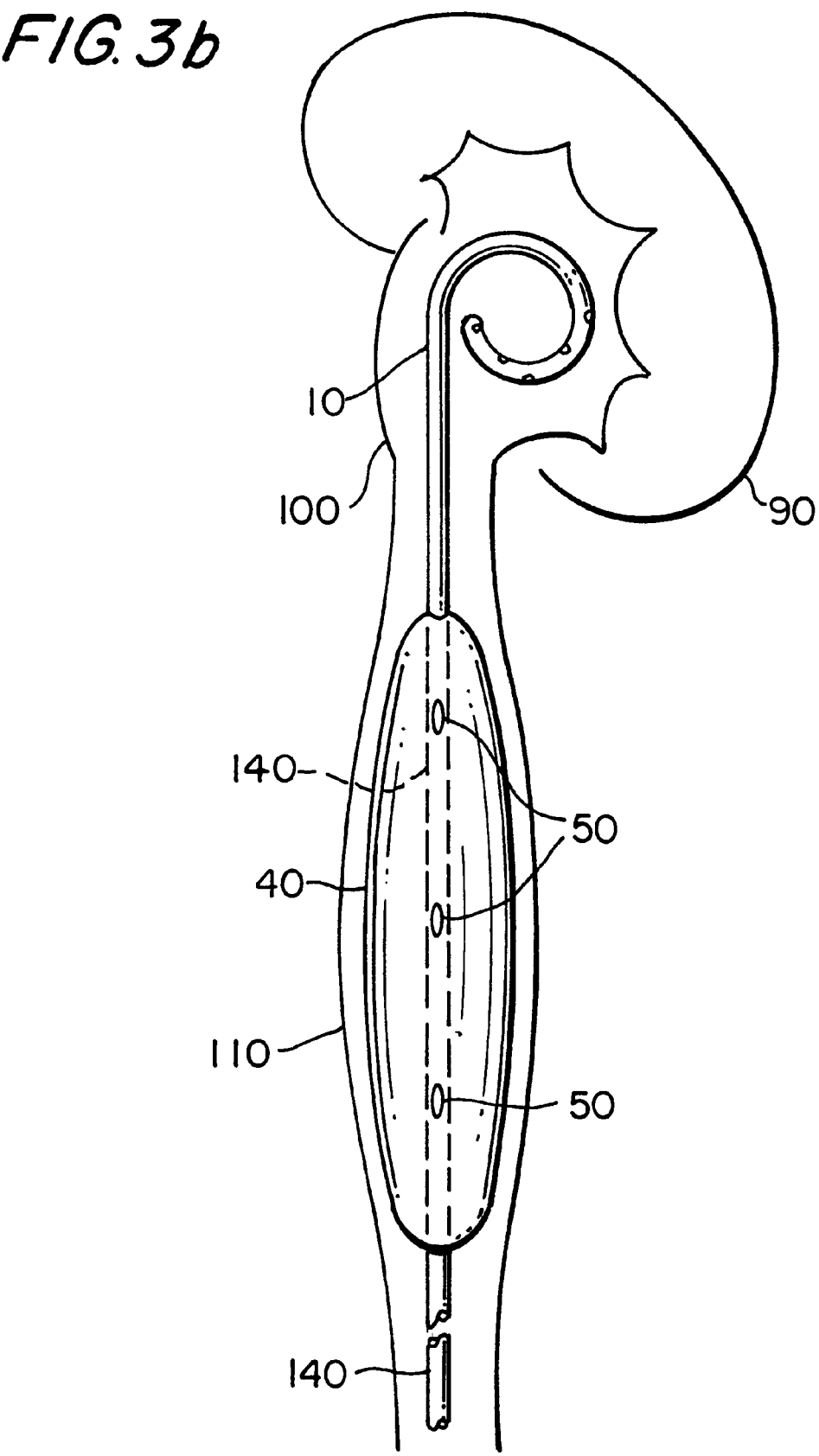

Once it is inserted into a patient, the tissue expander reservoir 40 is gradually expanded over a substantial period of time. Dependent upon the resulting megaureter required, such expansion can last from weeks to months. FIGS. 3*a* to 3*c* illustrate the combination urinary drainage tube and tissue expander as it would appear positioned in a human ureter. In one embodiment of the invention, sterile water combined with a radiologic contrast medium is injected into the tissue expander reservoir 40 via the tissue expander infusion port 80 with a syringe. Alternatively, the entire ureteral catheter may be made of a radiographically opaque substance. This allows the patient to undergo periodic x-ray evaluation of the tissue expander inflation process. Throughout this period, unobstructed drainage of urine from the kidney proceeds, thus preserving renal function. Once an acceptable volume and an acceptable megaureter has been produced, the tissue expander reservoir 40 is deflated and the ureteral catheter is removed. FIGS. 3*a* to 3*c* show the ureter 110 in progressive degrees of dilation corresponding to progressive degrees of the tissue expander reservoir 40 inflation. FIG. 3*a* shows the ureteral catheter after insertion and before expansion, FIG. 3*b* shows the ureteral catheter partially expanded, and FIG. 3*c* shows the ureteral catheter substantially expanded.

Figure 4A:
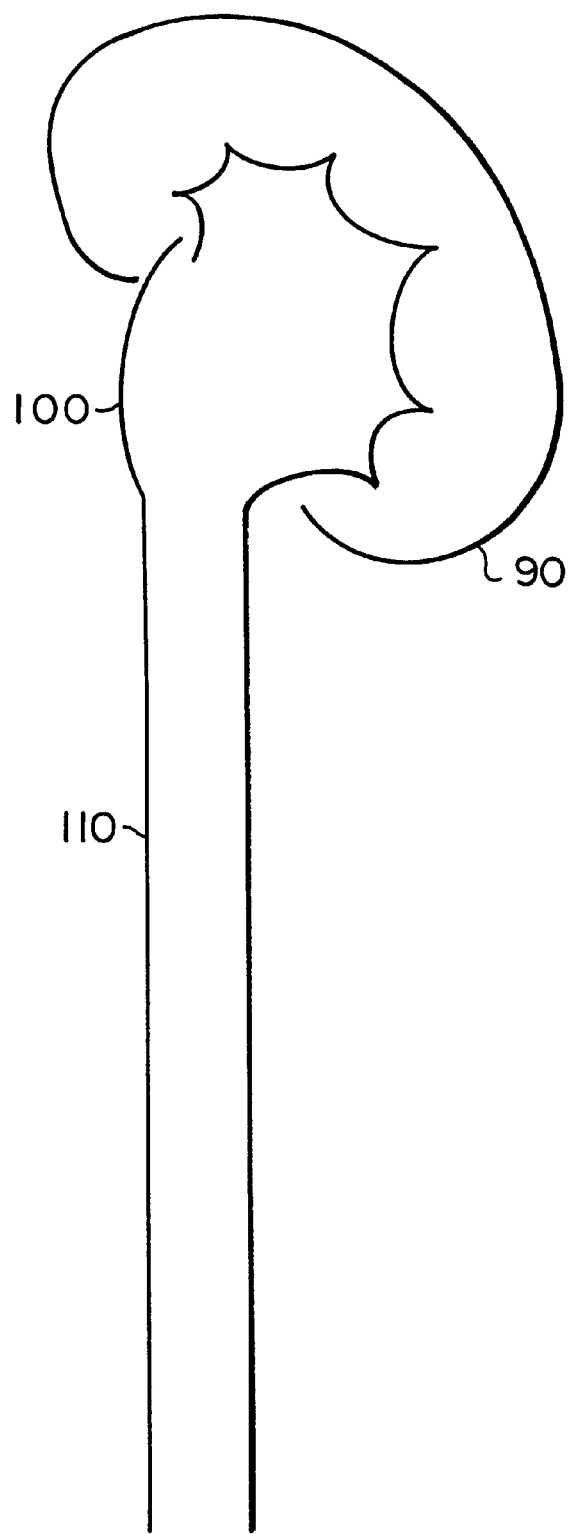
FIGS. 4a and 4b each represent a plan view of the urinary tract with the ureter before and after dilation, respectively.
Figure 4B:
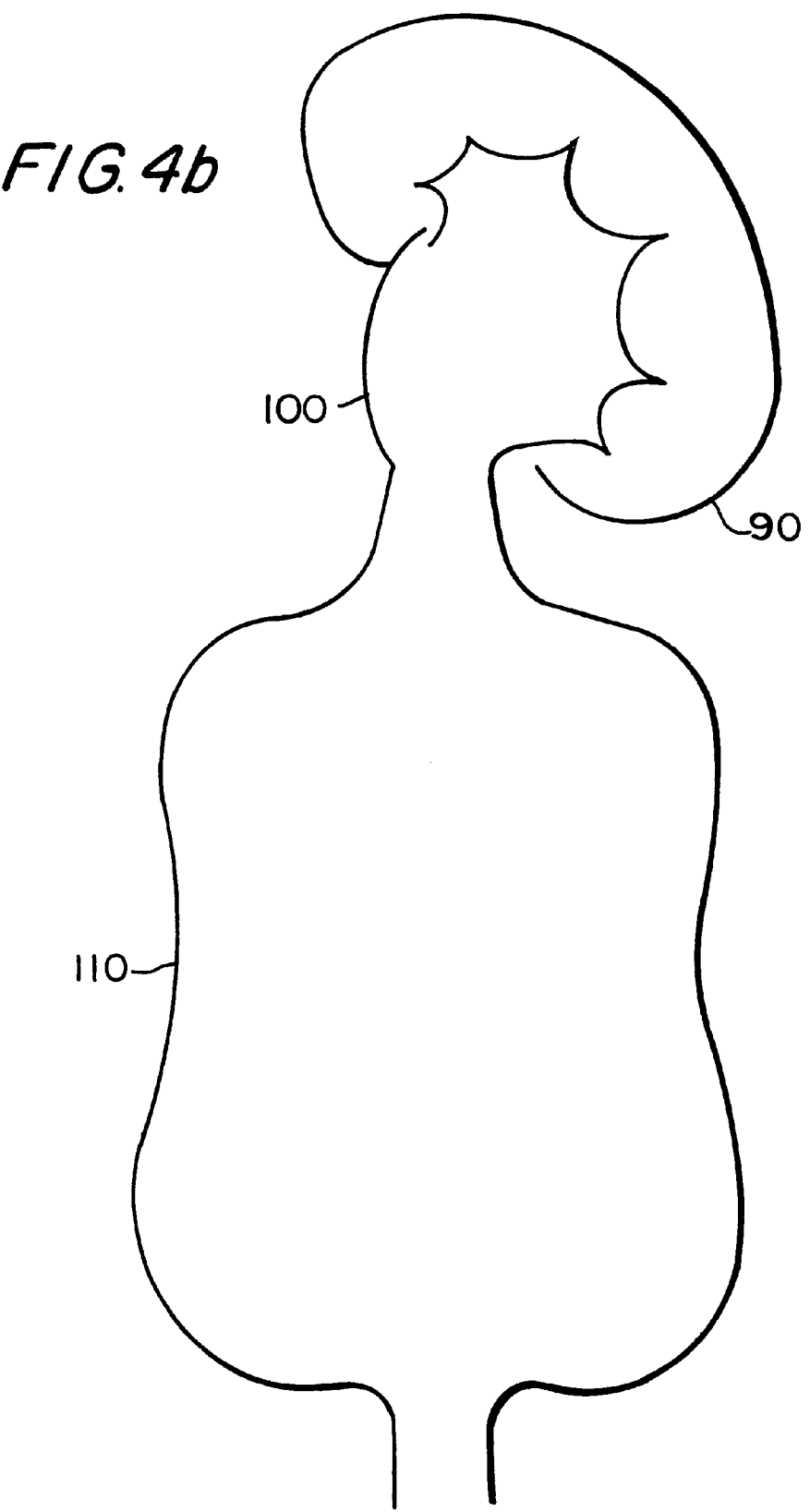

FIGS. 4*a* and 4*b* show the anatomy of the kidney 90, renal pelvis 100, and ureter 110 before and after dilation consistent with the varying degrees of expansion shown in FIGS. 3*a* and 3*c*. The resultant megaureter 110 is shown in FIG. 4*b* while the kidney 90 and renal pelvis 100 remain unchanged. The patient may now undergo surgical reconstruction of the urinary tract with native urothelium from the large redundant ureteral tissue produced by the expansion process.

The tissue expander reservoir 40 shown in the drawings preferably has at least a portion of its outer surface textured to provide physical surface interaction with the interior wall of the ureter. As the catheter of the invention provides that the reservoir can be positioned at the proximal, mid, or distal ureter portion, it is important that the ureter be held in place during the expansion process, which process can last for a matter of days or even weeks. Accordingly, the texture on the outer portion of the reservoir allows the reservoir to fully engage the ureter so as to obtain full expansion of the ureter. The texture of the reservoir does not substantially decrease the portion of the reservoir which contacts the ureter.

The ureteral catheter of the invention can be coated with any known, acceptable coating to ease insertion into the ureter. The coating is preferably a slippery, low friction lubrication such as a hydrophilic bond and covers at least a portion of the external surface of the catheter.

Figure 5:
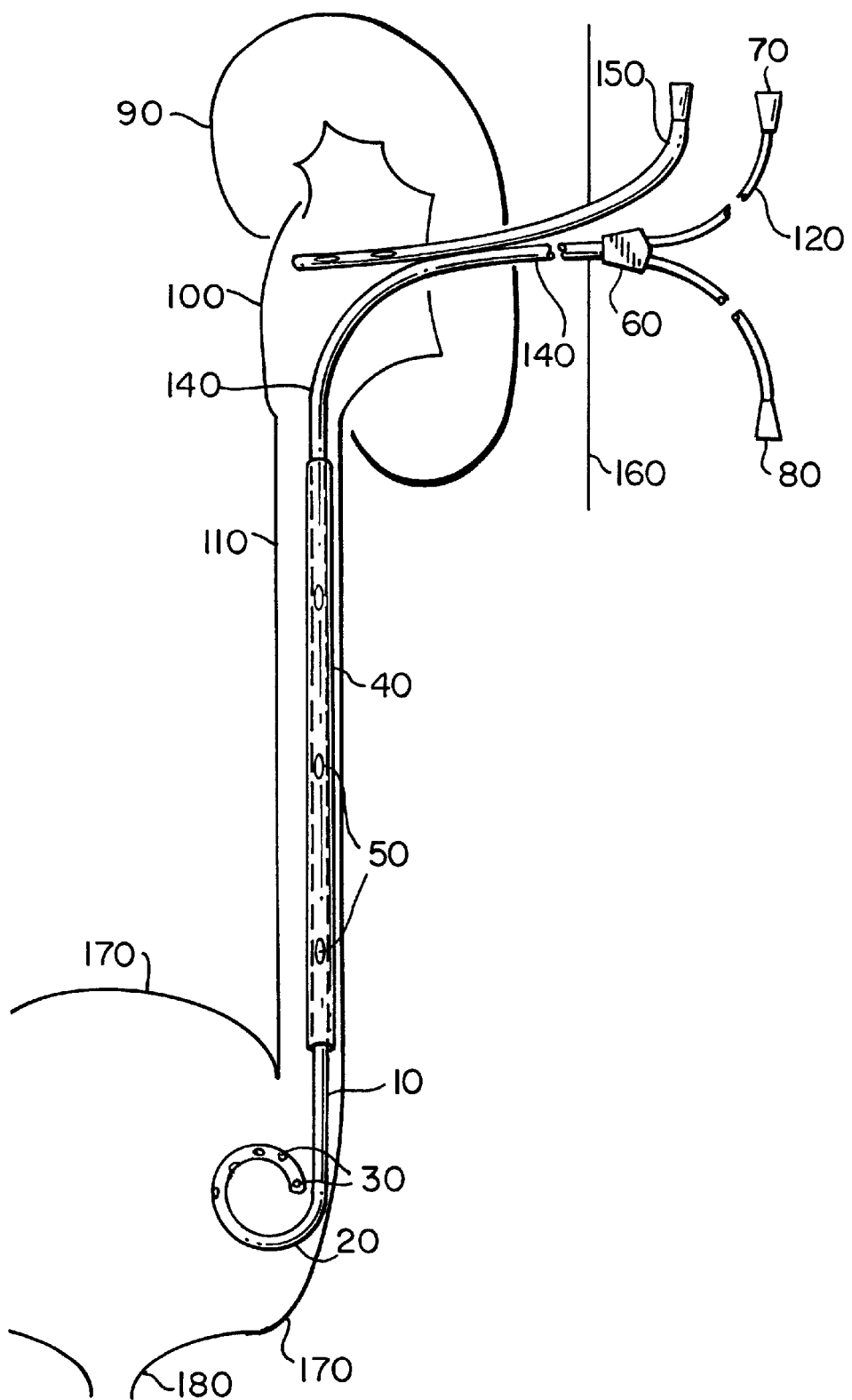
FIG. 5 represents a partly cross-sectional view of an embodiment of the invention with a single curl inserted into the urinary tract percutaneously through a nephrostomy tract adjacent a nephrostomy tube.

An alternative method of utilizing the combination urinary drainage tube and tissue expander is illustrated in FIG. 5. This alternative method involves placement of the apparatus percutaneously rather than transurethrally. In this alternative method, a nephrostomy tract, which is a path of communication between the skin of the patient's body wall 160 (usually in the back or flank area) and the renal pelvis 100, is produced. The combination urinary drainage tube and tissue expander is placed through the nephrostomy tract such that the distal urine drainage tube 10, with its curled end 20, is situated in the bladder 170. Under these circumstances, the combination urinary drainage tube and tissue expander no longer serve the purpose of draining urine. Rather, the flow of urine is diverted via the nephrostomy tract through a separate tube called a nephrostomy tube 150. The urine drainage port 70 is then capped while the tissue expander infusion port 80 is used as described above.

Optionally, the distal end of the ureteral catheter would be straight rather than curled. This configuration would be especially useful in certain situations, for example, where a patient has bladder cancer. It would be preferably to place the catheter through a nephrostomy, i.e., percutaneously through the back and kidney, with a straight catheter distal tip situated in the distal ureter and rather than the bladder. The reason for this is that a catheter placed into the bladder could possibly permit urine containing bladder cancer cells to communicate with the ureter and kidney.

In the embodiment discussed above, the ureteral catheter of the invention has been depicted and described with a curled distal end which acts as a means of retaining the urine drainage tube in the renal pelvis. Accordingly, the drainage tube needs to be in a straightened form for insertion through the ureter. For transurethral insertion of the ureteral catheter, the catheter can be straightened by threading a guidewire or stylet into the lumen of the urine drainage tube up to the end to the tube. When the urine drainage tube is positioned correctly, the guidewire or stylet is extracted.

Figure 6:
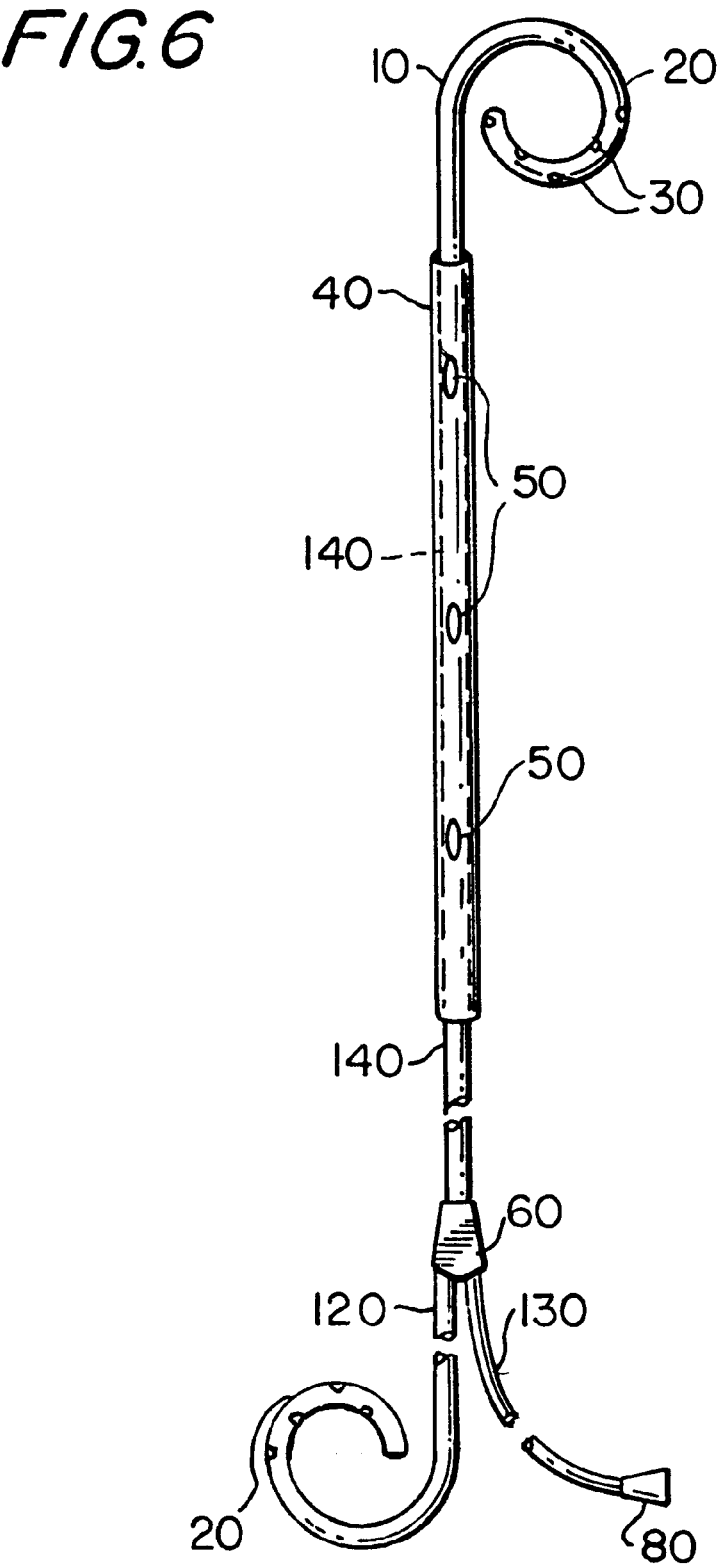
FIG. 6 represents a partly cross-sectional view of an embodiment of the invention with double curls.

An alternative embodiment of the combination urinary drainage tube and tissue expander of the invention is illustrated in FIG. 6. This alternative embodiment contains double curls, i.e., a curl 20 at the ends of both the distal urine drainage tube 10 and the proximal urine drainage tube 120. This embodiment may be installed either transurethrally (FIG. 7) or percutaneously (FIG. 8).

Figure 7:
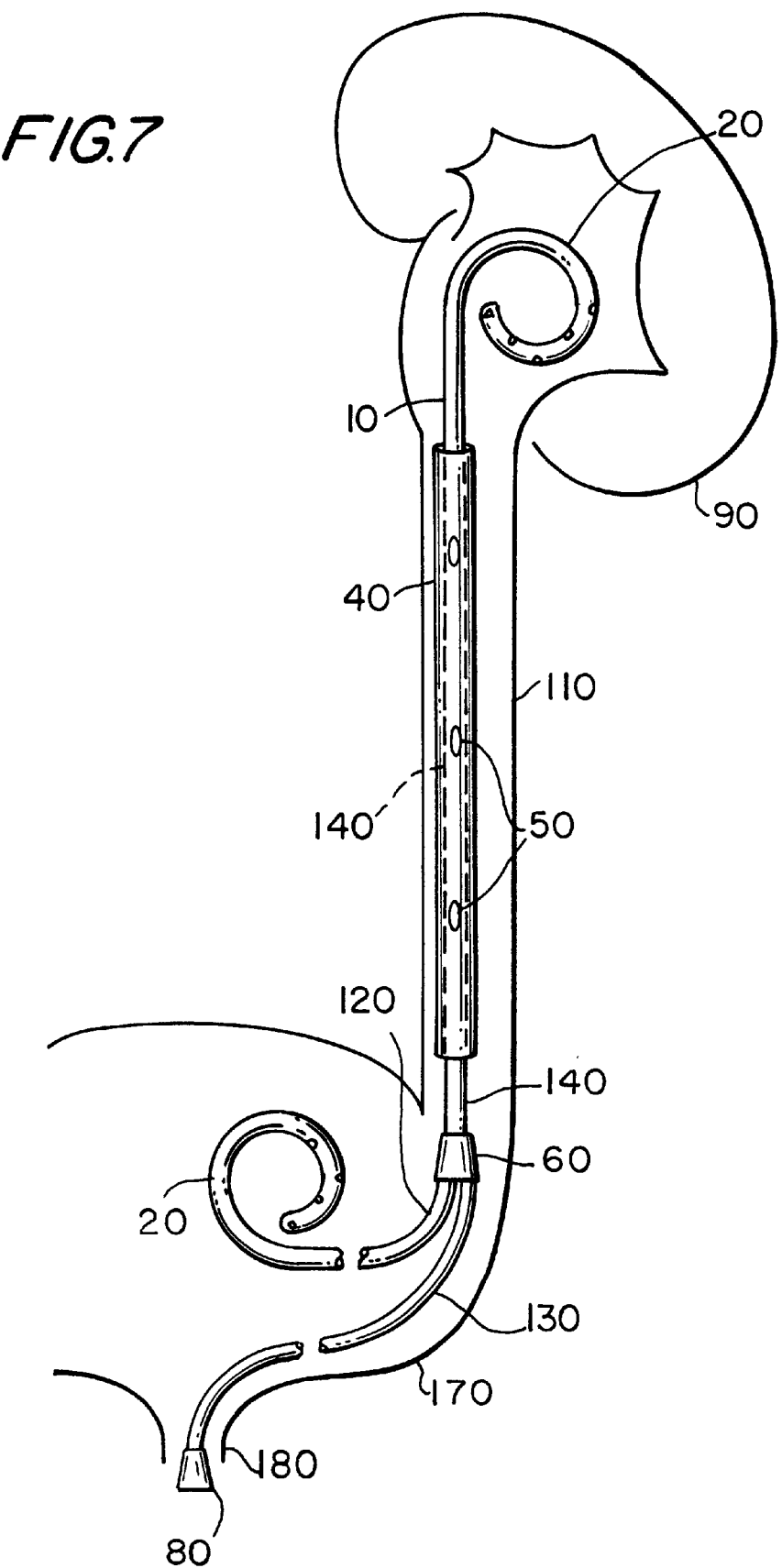
FIG. 7 represents an embodiment of FIG. 6 placed percutaneously through a nephrostomy tract.
Figure 8:
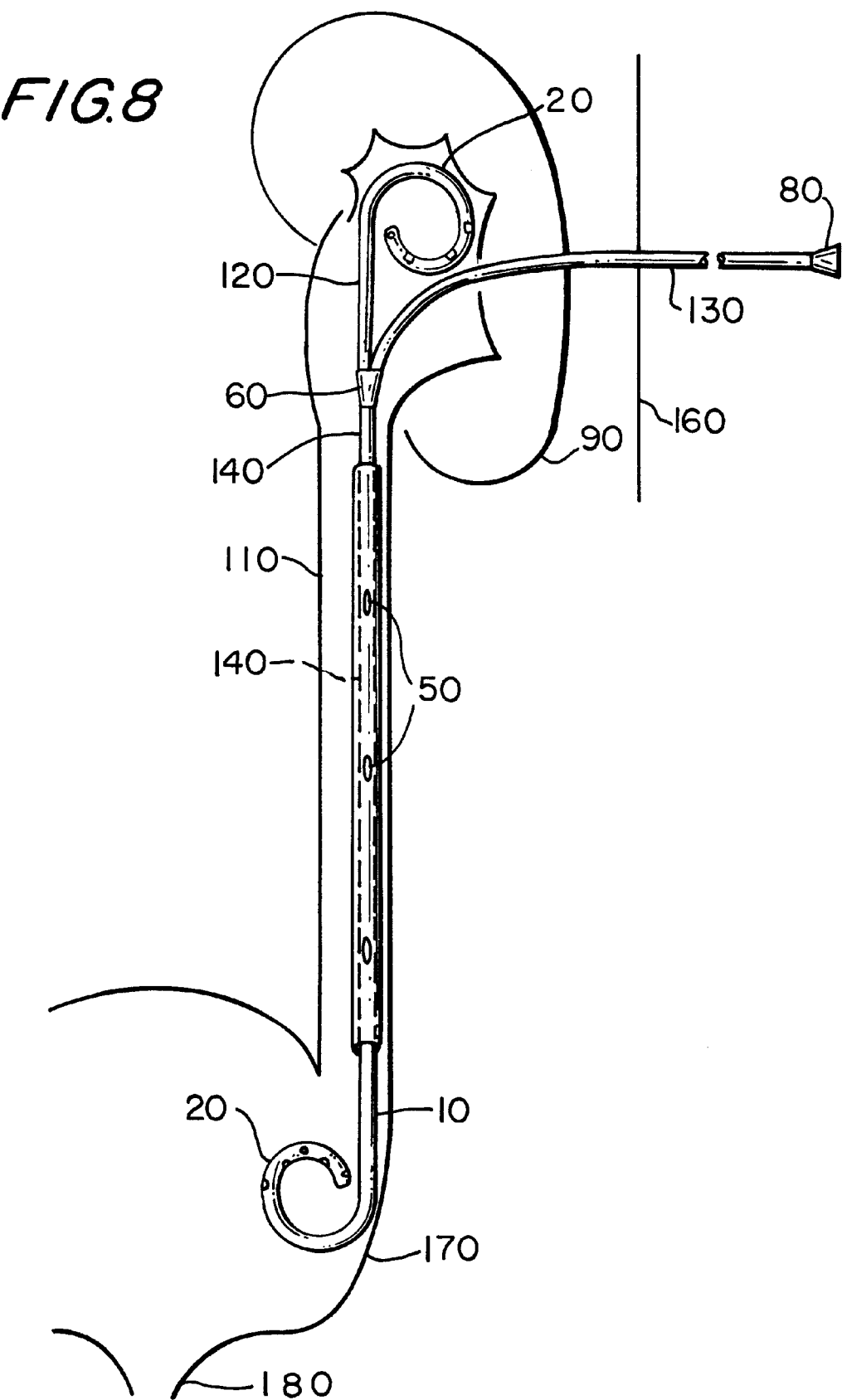
FIG. 8 represents a partly cross-sectional view of another embodiment of the invention.

In FIG. 7 the distal end of the drainage tube 20 is positioned in the renal pelvis, and the proximal end of the drainage tube is positioned in the bladder. In FIG. 8 the proximal end of the drainage tube 20 is positioned in the renal pelvis, and the distal end of the drainage tube positioned in the bladder. The advantage of the double curl embodiment is that the entire urine drainage tube may be positioned internally so that no urinary drainage port 70 is present. In this situation the patient would not need to wear a urinary drainage bag externally while undergoing the process of ureteral dilation, which could require weeks to months of time. Rather, with the double curl embodiment, the patient would store urine in the bladder and void per urethral. Moreover, this embodiment of the invention allows for drainage of urine into the bladder and then per urethra without the need of a nephrostomy tube as previously discussed when the catheter is used percutaneously. Accordingly, an additional tube is not required for percutaneous use with this embodiment.

The embodiment of the invention represented by FIG. 9 comprises a catheter 210 having a urine drainage lumen 220, a tissue inflation lumen 230, and an auxiliary lumen 240, which lumen are in fluid communication with ports 250, 260 and 270, respectively. Auxiliary lumen 240, which has distal openings 280 and, optionally, proximal openings 290, could be used by a clinician to infuse contrast material and take radiographs. Such radiographs could be helpful from a diagnostic and monitoring standpoint to assure the positioning of the catheter. When port 280 is stoppered, openings 280 and 270 could function with lumen 240 to provide an internal pathway for urine to drain into the native bladder or ureter rather than external drainage into a collection bag.

The description above should not be construed as limiting the scope of the invention to the specific embodiments described which are provided merely as illustrations. The scope of the invention encompasses interchangeable substitutions known by those skilled in the art. Many other variations are possible. It will be seen that the objects set forth above, among those made apparent from the preceding description, are efficiently attained and, since certain changes may be made in carrying out the method and in the apparatus set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features herein and described and all statements of the scope of the invention which, as a matter of language, might be said to fall therebetween.

REFERENCE NUMERALS IN DRAWINGS

10 Distal Urine Drainage Tube
20 Curled End
30 Urine Drainage Hole
40 Tissue Expander Reservoir
50 Tissue Expander Infusion Hole
60 Catheter Consolidation Site
70 Urine Drainage Port
80 Tissue Expander Infusion Port
90 Kidney
100 Renal Pelvis
110 Ureter
120 Proximal Urine Drainage Tube
130 Tissue Expander Conduit
140 Combined Urine Drainage Tube and Tissue Expander Conduit
150 Percutaneous Nephrostomy Tube
160 Patient's Body Wall
170 Bladder
180 Urethra
190 Urine Drainage Tube Lumen
200 Tissue Expander Conduit Lumen
210 Catheter
220 Drainage Lumen
230 Inflation Lumen
240 Auxiliary Lumen
250 Drainage Port
260 Inflation Port
270 Auxiliary Port
280 Distal Catheter Opening
290 Proximal Catheter Opening

What is claimed is:

1. A method of iatrogenically producing a megaureter without damage or injury to the associated kidney, which comprises the steps of:
   (a) positioning a ureteral catheter within the ureter, wherein said catheter comprises an tubular member having proximal and distal ends and an outer surface and having at least one drainage lumen therethrough, at least one inflation lumen, and a tissue expander reservoir sealingly attached to the outer surface of the tubular member and in fluid communication with said inflation lumen in the tubular member, wherein the distal end of the tubular member has a plurality of drainage holes in fluid connection with said drainage lumen; and
   (b) gradually expanding said tissue expander reservoir to iatrogenically produce a megaureter.

2. The method of iatrogenically producing a megaureter of claim 1, wherein said tubular member has a curl at both its proximal end and its distal end, both of said ends having a plurality of holes, and wherein the ureteral catheter is inserted percutaneously through a nephrostomy tract so that the distal end of the tubular member is in the bladder, the proximal end of the drainage tube is in the renal pelvis, and the reservoir is within the ureter.

3. The method of iatrogenically producing a megaureter of claim 1, wherein said tubular member has a curl at both its proximal end and its distal end, both of said ends having a plurality of holes so that the proximal end of the tubular member is in the bladder, the distal end of the tubular member is in the renal pelvis and the reservoir is within the ureter.

4. A method of iatrogenically producing a megaureter without damage or injury to the associated kidney, which comprises the steps of:
   (a) producing a nephrostomy tract between a patient's skin and the renal pelvis;
   (b) placing a combination ureteral catheter through the nephrostomy tract;
   wherein said catheter is comprised of an elongated flexible tubular member having proximal and distal ends and an outer surface and having at least one drainage lumen therethrough, at least one inflation lumen, and a tissue expander reservoir sealingly attached to the outer surface of the tubular member and in fluid communication with said inflation lumen in the tubular member, wherein the distal end of the tubular member has a plurality of drainage holes in fluid connection with said drainage lumen,
   wherein the catheter is positioned so that the distal end of a nephrostomy tube drains urine from the renal kidney and the expander reservoir is positioned within the ureter; and
   (c) gradually expanding said tissue expander reservoir to iatrogenically produce a megaureter.

5. A ureteral catheter for iatrogenically producing a megaureter, comprising
   (a) an elongated flexible tubular member having proximal and distal ends and an outer surface and having at least one drainage lumen therethrough and at least one inflation lumen; and
   (b) a tissue expander reservoir sealingly attached to the outer surface of the tubular member and in fluid communication with said at least one inflation lumen in the tubular member that extends from the tissue expander reservoir to an inflation port,
   wherein the proximal end of the drainage lumen is in fluid communication with a drainage port, wherein the distal end of the tubular member is curled, the drainage port comprises a curl, and each curl has a plurality of urine drainage holes to facilitate drainage into a patient's bladder, wherein the distal end of the tubular member plurality of drainage holes is in fluid connection with said at least one drainage lumen, and wherein the tissue expander reservoir can be expanded to iatrogenically produce a megaureter.

* * * * *